(12) United States Patent
Yamanaka et al.

(10) Patent No.: US 8,758,010 B2
(45) Date of Patent: Jun. 24, 2014

(54) DENTAL CLINICAL APPARATUS AND PLASMA JET APPLYING DEVICE FOR DENTISTRY

(75) Inventors: Michizo Yamanaka, Tokyo (JP); Tsuneo Kawahara, Tokyo (JP); Katsuhisa Kitano, Suita (JP); Satoshi Ikawa, Izumi (JP)

(73) Assignees: Yoshida Creation Inc., Tokyo (JP); Osaka University, Osaka (JP); Technology Research Institute of Osaka Prefecture, Osaka (JP)

( * ) Notice: Subject to any disclaimer, the term of this patent is extended or adjusted under 35 U.S.C. 154(b) by 378 days.

(21) Appl. No.: 13/054,386

(22) PCT Filed: Jul. 17, 2009

(86) PCT No.: PCT/JP2009/062937
§ 371 (c)(1),
(2), (4) Date: Apr. 5, 2011

(87) PCT Pub. No.: WO2010/008062
PCT Pub. Date: Jan. 21, 2010

(65) Prior Publication Data
US 2011/0183284 A1 Jul. 28, 2011

(30) Foreign Application Priority Data
Jul. 18, 2008 (JP) .................... 2008-187564

(51) Int. Cl.
*A61C 17/00* (2006.01)
*A61C 5/04* (2006.01)
*A61C 3/00* (2006.01)

(52) U.S. Cl.
USPC ............... 433/89; 433/80; 433/216; 433/141

(58) Field of Classification Search
USPC ............ 433/29–32, 80–82, 87–90, 103–105, 433/114, 215–216, 224, 141–144; 601/162–165; 401/171–180; 222/63, 222/333, 386, 253, 263, 386.5; 219/121.36, 219/121.47, 121.48, 121.5, 121.52; 313/231.41, 111.21, 111.31; 315/111.01, 111.21, 111.31, 111.71, 315/111.91
See application file for complete search history.

(56) References Cited

U.S. PATENT DOCUMENTS 5,120,219 A * 6/1992 De Farcy ....................... 433/88
5,831,238 A * 11/1998 Takuya et al. ............ 219/121.59
7,179,526 B2 * 2/2007 Rosenflanz et al. .......... 428/329
(Continued)

FOREIGN PATENT DOCUMENTS

JP 63-085214 6/1988
JP 7-308381 11/1995
(Continued)

*Primary Examiner* — Yogesh Patel
(74) *Attorney, Agent, or Firm* — Jordan and Hamburg LLP (57) ABSTRACT

A dental clinical apparatus having a function which conventional instruments for dental treatment have not had and having a novel constitution. The dental clinical apparatus includes a syringe which has a fluid jetting system for dental treatment and a plasma jet applying means for producing a plasma jet from the end by allowing a low-frequency high-voltage power supply to apply a low-frequency high voltage between electrodes on the outer peripheral surface of a rare gas tube through which a rare gas having a low dielectric breakdown voltage under the atmospheric pressure is flowed, and thereby causing electrical discharge.

11 Claims, 8 Drawing Sheets

(56) References Cited

U.S. PATENT DOCUMENTS

| | | | |
|---|---|---|---|
| 7,608,839 B2* | 10/2009 | Coulombe et al. | 250/426 |
| 8,232,729 B2* | 7/2012 | Kitano et al. | 315/111.21 |
| 2005/0250070 A1* | 11/2005 | Hamman | 433/88 |
| 2006/0084158 A1 | 4/2006 | Viol | |
| 2006/0091117 A1* | 5/2006 | Blankenship et al. | 219/121.47 |
| 2007/0029500 A1* | 2/2007 | Coulombe et al. | 250/423 F |
| 2007/0224571 A1* | 9/2007 | Watson | 433/31 |

FOREIGN PATENT DOCUMENTS

| | | |
|---|---|---|
| JP | 2005-073819 | 3/2005 |
| JP | 2005-253849 | 9/2005 |
| JP | 2006-526442 | 11/2006 |
| WO | WO-2008/072390 | 6/2008 |
| WO | WO-2009/041049 | 4/2009 |

* cited by examiner

DENTAL CLINICAL APPARATUS AND PLASMA JET APPLYING DEVICE FOR DENTISTRY

BACKGROUND OF THE INVENTION

The present invention relates to a dental clinical apparatus and a plasma jet applying device for dentistry.

It is widely known that in the dental care, generally, a dental syringe and a cutting tool, such as a dental turbine, a dental micromotor or a scaler, are often used. On the other hand, in the field of plasma technology, a plasma applying apparatus as providing a method of enhancing the wettability of a material surface to thereby increase an adhesion strength is being marketed by companies, for example, Nihon Plasmatreat Inc.

Patent reference 1 discloses, as one form of syringe, a medical spray syringe that, for example, can prevent any leakage of liquid from areas other than the distal end of a nozzle and can facilitate the attachment and detachment of a supply tube.

Patent reference 2 discloses, as one form of cutting tool, a handpiece for medical dental use that can prevent any rolling of a rotating tool or vibratory tool.

Meanwhile, nonpatent references 1 and 2 disclose researches on the conversion of a rare gas to plasma by use of a low-frequency high-voltage power supply, researches on the plasma sterilization in liquids, etc.

Patent reference 1: JP H07-308381 A,
Patent reference 2: JP 2005-253849 A,
Nonpatent reference 1: Ministry of Education, Culture, Sports, Science and Technology: Grants for Science: Grant-in-Aid for Scientific Research on Priority Areas: 2007 Working Papers: Published on Jun. 1, 2008: A01-(6) "Generation and analysis of advanced reaction field by in-liquid glow plasma" Research representative: Katsuhisa Kitano, and
Nonpatent reference 2: Ministry of Education, Culture, Sports, Science and Technology: Grants for Science: Grant-in-Aid for Scientific Research on Priority Areas: 2008 Working Papers: Published on Feb. 26, 2007: A01-(6) "Generation and analysis of advanced reaction field by in-liquid glow plasma" Research representative: Katsuhisa Kitano.

SUMMARY OF THE INVENTION

The present invention has been made in view of the above background art. It is an object of the present invention to provide a dental clinical apparatus of novel structure with hitherto unknown functions, taking into consideration instruments for dental treatment in combination with the plasma research results disclosed in nonpatent reference 1.

The most characteristic feature of the dental clinical apparatus of the present invention is that the dental clinical apparatus comprises an instrument for dental treatment fitted with a plasma jet applying means to thereby realize application of a plasma jet to an affected area during treatment.

In the present invention, the expression "syringe" is defined as a means for the injection, application and vacuum suctioning of a gas, a liquid, light or a plasma jet. The expression "plasma jet" is defined as a plasma applied from an application means.

A first aspect of the invention provides a dental clinical apparatus comprising an instrument for dental treatment fitted with a plasma jet applying means to thereby realize application of a plasma jet to an affected area during treatment. Therefore, there can be provided a dental clinical apparatus capable of attaining the improvement of the wettability of an affected area during treatment, and also the sterilization of an affected area during treatment, by plasma jet application.

A second aspect of the invention provides a dental clinical apparatus comprising a syringe employed as the instrument. Therefore, there can be provided a dental clinical apparatus capable of attaining the improvement of the wettability of an affected area during treatment, and also the sterilization of an affected area during treatment, by plasma jet application.

A third aspect of the invention provides a dental clinical apparatus comprising a syringe employed as the instrument, the syringe configured to be capable of outputting air, water, a medicinal liquid, a washing liquid, light and a plasma jet individually or in a combination of a plurality thereof. Therefore, there can be provided a dental clinical apparatus capable of realizing a variety of treatments to an affected area during treatment by a combination of the function of syringe per se with the function of applied plasma jet. Moreover, there can be provided a dental clinical apparatus capable of enhancing the wettability of a tooth surface and thus performing a photopolymerization strengthening the adhesion of a resin by a combination of light (especially light with a wavelength capable of hardening a resin as a dental restorative material) with plasma jet application.

A fourth aspect of the invention provides a dental clinical apparatus comprising a cutting tool employed as the instrument. Therefore, there can be provided a novel dental clinical apparatus capable of plasma jet application exerting the above effects simultaneously with cutting of teeth or tartar, or before or after the cutting.

A fifth aspect of the invention provides a dental clinical apparatus in which a dental turbine, or a dental micromotor or a scaler is the instrument cutting tool.

A sixth aspect of the invention provides a dental clinical apparatus comprising a cutting tool, as the instrument, configured to be capable of outputting air, water, a medicinal liquid, a washing liquid, light and a plasma jet individually or in a combination of a plurality thereof. Therefore, there can be provided a dental clinical apparatus capable of realizing a variety of treatments to an affected area during treatment by a combination of the perforation and other functions of the cutting tool per se with the function of applied plasma jet.

A seventh aspect of the invention provides a dental clinical apparatus wherein the cutting tool as the instrument is equipped with a root canal length measuring means for measuring the length of the root canal so that the cutting tool has its driving force changed in accordance with the measurement value of the length of the root canal. Therefore, there can be provided a dental clinical apparatus capable of carrying out appropriate treatment of the root canal.

An eighth aspect of the invention provides a dental clinical apparatus wherein the instrument is equipped with a washing liquid supply means capable of supplying a washing liquid to the affected area after elimination of a decay lesion from a tooth surface. Therefore, there can be provided a dental clinical apparatus capable of efficiently carrying out the elimination and washing of a decay lesion, the application of plasma jet to the affected area during treatment, etc.

A ninth aspect of the invention provides a dental clinical apparatus that permits choosing of the application of plasma jet to the affected area during treatment in the use of the instrument in treatment of the root canal interior after elimination of a decay lesion.

Tenth and eleventh aspects of the invention provide a dental clinical apparatus wherein the instrument is equipped with a desmearing treatment means for the dissolution and washing of smear plug in the root canal interior after elimination of a decay lesion from a tooth so that the plasma jet application can be realized after or during the treatment by the desmearing treatment means. Therefore, there can be provided a dental clinical apparatus capable of efficiently carrying out the sterilization of the root canal interior by the application of plasma jet.

Twelfth and thirteenth aspects of the invention provide a dental clinical apparatus wherein the plasma jet applying means of the instrument has a plasma jet application orifice provided at its distal end with a distal end nozzle having an arbitrary distal end morphology or with any of distal end nozzles being different from each other in inside diameters. Therefore, there can be provided a dental clinical apparatus that permits varied choice of the morphology of the plasma jet application area to an affected area during treatment with the result that the optimization of the plasma jet application area and an enhancement of treatment efficiency can be attained.

A fourteenth aspect of the invention provides a dental clinical apparatus wherein the plasma jet applying means fitted to the instrument is configured so that by means of a low-frequency high-voltage power supply, electrical discharge is carried out on an outer circumference of a dielectric tube or metal tube through which a rare gas exhibiting a low dielectric breakdown voltage under atmospheric pressure flows, thereby generating a plasma jet from an distal end thereof. Therefore, there can be provided a dental clinical apparatus capable of exerting the above effects.

A fifteenth aspect of the invention provides a dental clinical apparatus wherein gaseous helium or gaseous argon is employed as the rare gas exhibiting a low dielectric breakdown voltage which is the source of plasma jet generation in the plasma jet applying means. Therefore, there can be provided a dental clinical apparatus capable of exerting the above effects.

A sixteenth aspect of the invention provides a dental clinical apparatus wherein the plasma jet applying means fitted to the instrument has a one-electrode structure. Therefore, there can be provided a dental clinical apparatus capable of exerting the above effects.

A seventeenth aspect of the invention provides a dental clinical apparatus wherein the plasma jet applying means having a one-electrode structure is provided at its grounded portion with a wear means which a patient can wear. Therefore, there can be provided a dental clinical apparatus configured to utilize a portion of the body of the patient for grounding and capable of exerting the above effects.

An eighteenth aspect of the invention provides a dental clinical apparatus wherein the plasma jet applying means fitted to the instrument has a two-electrode structure. Therefore, there can be provided a dental clinical apparatus capable of exerting the above effects.

Nineteenth and twentieth aspects of the invention provide a dental clinical apparatus wherein the plasma jet applying means fitted to the instrument has a cordless structure having a high-pressure cylinder, a high voltage boosting circuit and a dry-cell battery housed therein. Therefore, there can be provided a simplified dental clinical apparatus that allows the instrument alone to generate the plasma to be applied to an affected area during treatment and conduct treatment.

A twenty-first aspect of the invention provides a dental clinical apparatus based on that of the fourteenth or fifteenth aspect of the invention wherein a gas supply passage is provided with a gas fluid regulating valve. Therefore, there can be provided a dental clinical apparatus that facilitates changing the length and application intensity of the plasma jet generated by plasma jet applying means 4, thereby making it easy to cope with various morphologies of an affected area during treatment.

A twenty-second aspect of the invention provides a dental clinical apparatus based on that third or eleventh aspect of the invention wherein a liquid supplied as the water, the medicinal liquid such as a desmearing medicinal liquid or the washing liquid exhibits a pH value of 4.5 or below. Therefore, there can be provided a dental clinical apparatus capable of effective sterilization at an affected area.

A twenty-third aspect of the invention provides a plasma jet applying device for dentistry comprising a device main body having the shape of a syringe as an instrument fitted with a plasma jet applying means configured so that by means of a low-frequency high-voltage power supply, a two-electrode electric discharge is performed on an outer circumference of a dielectric tube or metal tube through which a gas from a high-pressure cylinder flows to thereby generate a plasma jet from a distal end thereof. Therefore, there can be provided a plasma jet applying device for dentistry capable of improving the wettability for resin filling at an affected area during treatment and capable of sterilization at an affected area during treatment, which plasma jet applying device for dentistry is cordless and permits arbitrary carrying to thereby render it simple and easy to use the same in combination with any of existing syringes and cutting tools for dental treatment.

A twenty-fourth aspect of the invention provides a plasma jet applying device for dentistry comprising a plasma jet applying means with one-electrode structure.

A twenty-fifth aspect of the invention provides a plasma jet applying device for dentistry capable of not only sterilizing an affected area during treatment but also enhancing the wettability of a tooth surface and thus effecting a photopolymerization increasing the adhesion strength of a resin by a combination of light (especially light with a wavelength capable of hardening a resin as a dental restorative material) with plasma jet application.

A twenty-sixth aspect of the invention provides a plasma jet applying device for dentistry capable of, while suctioning saliva and dust from the oral cavity by vacuum, enhancing the wettability of an affected area during treatment and further sterilizing the same by plasma jet application.

The dental clinical apparatus of the present invention realizes a dental clinical apparatus of hitherto unknown novel structure by comprising a syringe as an instrument for dental treatment fitted with a plasma jet applying means configured so that by means of a low-frequency high-voltage power supply, electrical discharge is carried out on an outer circumference of a dielectric tube or metal tube through which a rare gas exhibiting a low dielectric breakdown voltage under atmospheric pressure flows, thereby generating a plasma jet from an distal end thereof.

Now, the dental clinical apparatuses according to Embodiments of the present invention will be described in detail with reference to the appended drawings.

EMBODIMENT 1

Figure 1:
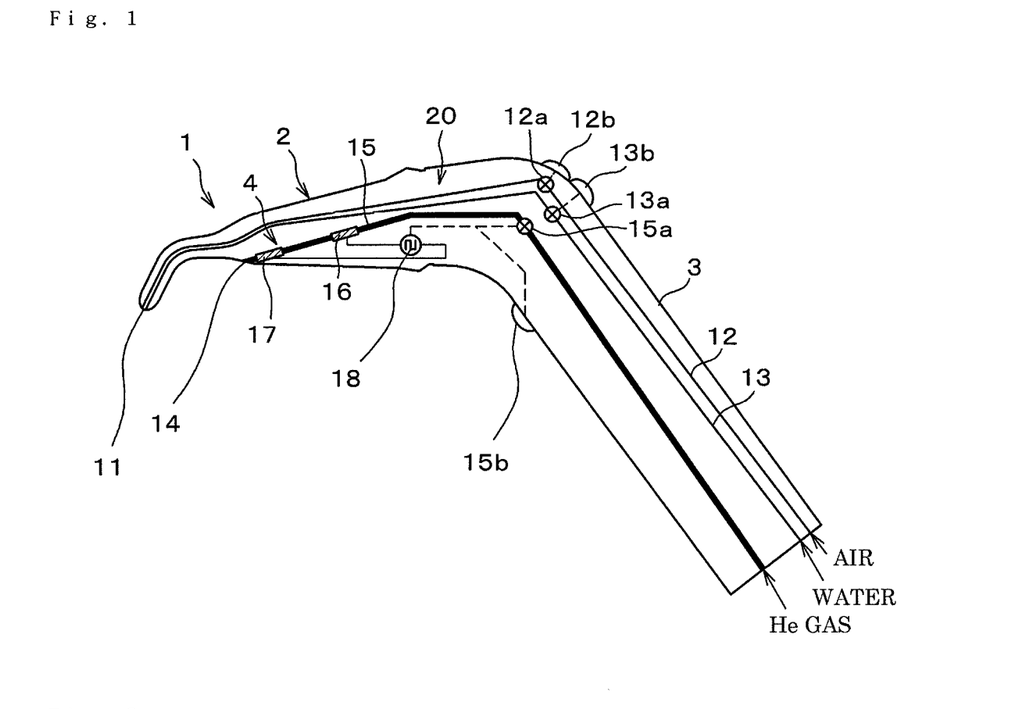
FIG. 1 is a schematic configuration view of a syringe-shaped dental clinical apparatus according to Embodiment 1 of the present invention.

Referring to FIG. 1, the dental clinical apparatus 1 according to Embodiment 1 is characterized by including a syringe 2, as an instrument, composed mainly of a hand-graspable metallic material bent and formed into an approximately ←-shape, the syringe 2 fitted in its main body 3 with a 2-electrode plasma jet applying means 4 capable of applying to an affected area during treatment of a tooth or the like a plasma based on a rare gas, such as gaseous helium or gaseous argon, exhibiting a low dielectric breakdown voltage under atmospheric pressure, which plasma has the capabilities of enhancing the wettability of the affected area during treatment and sterilizing the same and the like.

The main body 3 of the syringe 2 is provided at its distal end side with an emission orifice 11 for air and water (or a medicinal liquid, a washing liquid such as distilled water, etc.). The main body 3 is further provided with an air conduit 12 and a liquid conduit 13 both extending from the proximal end side of the main body 3 through the interior thereof to the emission orifice 11. Accordingly, air is fed through the air conduit 12 to the emission orifice 11, and selective feeding of water, a medicinal liquid, a washing liquid or the like is conducted through the liquid conduit 13 to the emission orifice 11. These elements construct a fluid jetting system 20.

Thus, there are provided means for selective emission of a spray of water, water with air or water-air mixture, emission of a medicinal liquid and emission of a washing liquid from the emission orifice 11 to an affected area during treatment.

A plasma jet applying means 4 is housed in the main body 3, so that from a plasma jet application orifice 14 disposed in the vicinity of the emission orifice 11 in the main body 3, a plasma jet is applied in substantially the same direction as that of water or the like emitted from the emission orifice 11.

The plasma jet applying means 4 includes a rare gas tube 15 selected from among dielectric tubes, such as a glass tube, a resin tube and a ceramic tube, which has an inside diameter of about several millimeters and extends from the proximal end side of the main body 3 through the interior thereof to the plasma jet application orifice 14, two electrodes 16,17 and a low-frequency high-voltage power supply 18.

On-off valves 12a, 13a, 15a each consisting of, for example, an electromagnetic valve are connected to the air conduit 12, liquid conduit 13 and rare gas tube 15, respectively.

Further, the main body 3 is provided on its outer circumference portion with an air switch 12b, a liquid switch 13b and a plasma generation switch 15b, so that air supply/discontinuation, the supply/discontinuation of water or the like and plasma generation/discontinuation can be operated thereby. In this Embodiment, the air conduit 12, liquid conduit 13 and rare gas tube 15 are provided separately from each other. Instead, switched supply of air, a liquid or a rare gas may be performed by sharing only one rare gas tube 15.

Below, the plasma jet applying means 4 will be described in detail with reference to FIG. 2.

Figure 2:
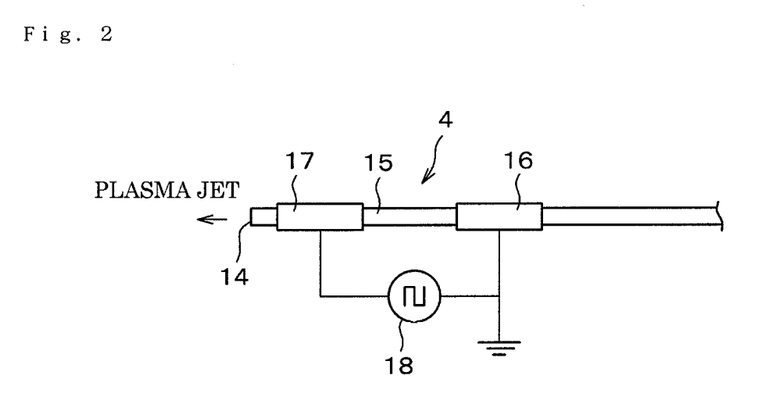
FIG. 2 is an enlarged explanatory view of a plasma jet generating means included in a dental clinical apparatus according to Embodiment 1.

In the plasma jet applying means 4, referring to FIG. 2, two electrodes 16,17 are coaxially disposed with a spacing of, for example, about several tens of millimeters on an upstream side and a downstream side along a rare gas tube 15 through which gaseous helium as one of rare gases flows. A low-frequency high-voltage power supply 18 capable of outputting, for example, about 10 kHz-10 kV is connected to the two electrodes 16,17, so that low-frequency high-voltage is applied to the two electrodes 16,17. The side of the upstream electrode 16 is grounded to the main body 3. Namely, the downstream electrode 17 provides a high-voltage electrode.

A plasma jet is generated by dielectric barrier electric discharge between the two electrodes 16,17 in the rare gas tube 15. The generated plasma jet is emitted from the plasma jet application orifice 14, and is applied to an affected area during treatment.

An example of particular structure of the plasma jet application orifice 14 will be described below with reference to FIG. 3.

Figure 3:
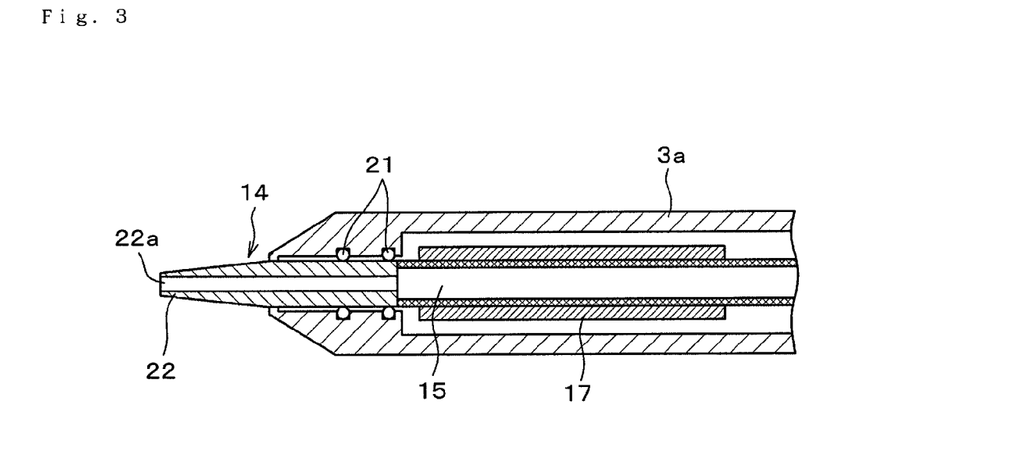
FIG. 3 is a partial enlarged sectional view of one form of tip nozzle as a constituent of a plasma jet application orifice included in a dental clinical apparatus according to Embodiment 1.

The plasma jet application orifice 14 can have such a structure that referring to FIG. 3, a tip nozzle 22 provided with a circular hole 22a by boring is detachably fitted through an O-ring 21 into a receiving portion 3a provided in the main body 3 of the syringe 2.

In this structure, by appropriate changing and setting of the inside diameter of the circular hole 22a to, for example, 50 μm or 100 μm, a desirable circular morphology with varied diameter can be selected as the area of plasma jet application from the tip nozzle 22 to an affected area during treatment. Therefore, coping with various morphologies of an affected area during treatment can be facilitated.

Figure 4:
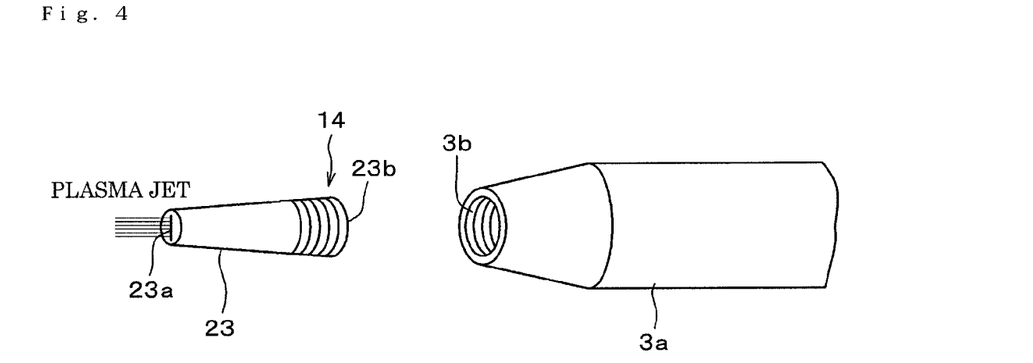
FIG. 4 is a partial enlarged sectional view of another form of tip nozzle as a constituent of a plasma jet application orifice included in a dental clinical apparatus according to Embodiment 1.

Further, the plasma jet application orifice can have such a structure that referring to FIG. 4, a threaded portion 23b made on a tip nozzle 23 provided at its application end with an opening portion 23a of, for example, thin rectangular shape is screwed into a threaded portion 3b of the receiving portion 3a provided in the main body 3 to thereby fit the tip nozzle to the main body to thereby attain fitting thereof.

In this structure, a plasma jet can be applied from the tip nozzle 23 to an affected area during treatment while forming a plasma application area having the shape of a sheet of, for example, 10 mm×2 mm or 20 mm×3 mm (thin rectangular). Therefore, coping with various morphologies of an affected area during treatment can be facilitated.

Figure 5:
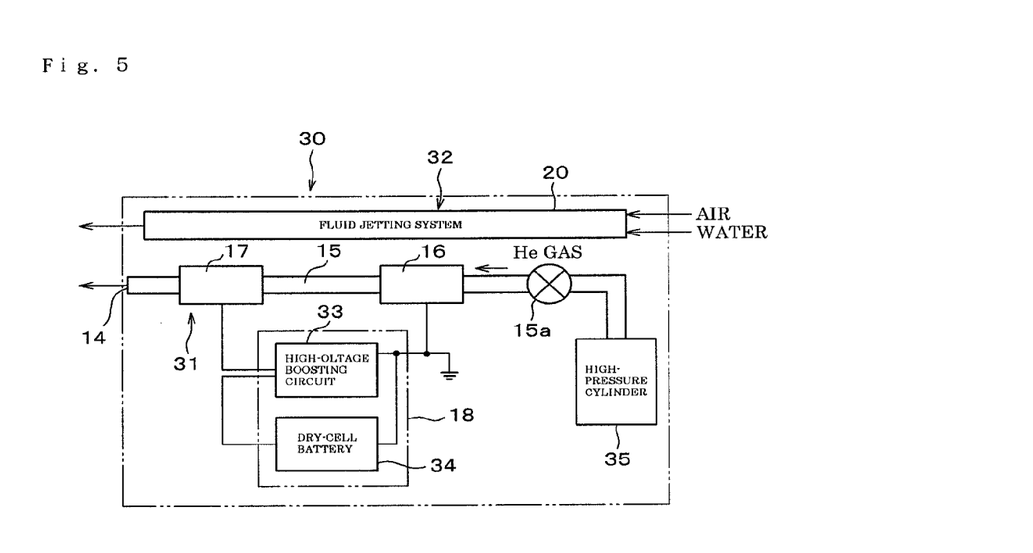
FIG. 5 is a schematic configuration view of a plasma jet applying means of cordless structure included in a dental clinical apparatus according to Embodiment 1.

Now, referring to FIG. 5, a syringe 30 having the plasma jet applying means 4 changed to a cordless structure will be briefly described.

The syringe 30 includes a main body 32 of, for example, hair dryer morphology which has not only the above-mentioned fluid jetting system 20 assembled therein but also a plasma jet applying means 31 fitted thereto.

In the plasma jet applying means 31, two electrodes 16,17 are disposed with a given spacing on the same rare gas tube 15 as mentioned above. A low-frequency high-voltage power supply 18 including a high voltage boosting circuit 33 capable of outputting, for example, about 10 kHz-10 kV and a dry-cell battery 34 capable of outputting DC 9V is connected to the two electrodes 16,17, so that low-frequency high-voltage is applied to the two electrodes 16,17. The side of the upstream electrode 16 is grounded to the main body 32. Further, a high-pressure cylinder 35 capable of supplying gaseous helium or gaseous argon housed therein is fitted to the rare gas tube 15.

The syringe 30 equipped with the plasma jet applying means 31 having a cordless structure of the above arrangement does not need to connect a rare gas supply piping to the rare gas tube 15 of the plasma jet applying means 31, apart from the piping to the fluid jetting system 20, so that there can be provided a simple apparatus capable of generating a plasma jet to be applied to an affected area during treatment and treating the same by use of the syringe 30 alone.

Figure 6:
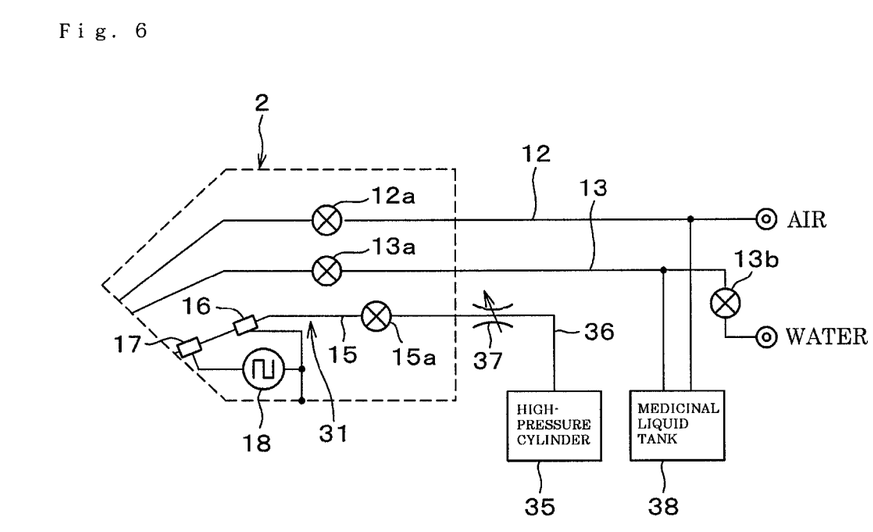
FIG. 6 is a schematic configuration view of a dental clinical apparatus including a two-electrode plasma jet applying means according to Embodiment 1, additionally provided with a gas fluid regulating valve.

FIG. 6 shows a schematic example of arrangement in which a gas fluid regulating valve 37 is fitted to the midstream of a supply conduit 36 from the high-pressure cylinder 35 for supply of a rare gas to the rare gas tube 15 of the syringe 2 of FIG. 1.

A medicinal liquid (or a washing liquid) is supplied by a medicinal liquid tank 38 to the air conduit 12 and the liquid conduit 13. In FIG. 6, mark 13b denotes an on-off valve.

The medicinal liquid to be placed in the medicinal liquid tank 38 is, for example, a desmearing medicinal liquid inclusive of an organic acid such as citric acid, phosphoric acid or formic acid, a mixture of sodium hypochlorite and EDTA aqueous solutions, etc.

For example, dental caries (tooth decay) is caused by an organic acid produced from a sugar component of food by microbes, such as streptococcus and lactic-acid bacillus, contained in food, tooth structure and plaque.

In the progression of dental caries, caries C3 denotes the reaching of dental caries to the pulp, and caries C4 denotes the stage in which the crown portion is dissolved away while the root portion remains.

In the stage of these caries C3 and caries C4, a desmearing medicinal liquid is used to remove any smear layer accumulated on a tooth root surface and any smear plug penetrated in the dental tubule.

In Embodiment 1, use is made of a desmearing medicinal liquid of 4.5 or below pH value in order to enhance its bactericidal capacity.

In this respect, reference can be made to the description relating to the effect of coliform sterilization by plasma application appearing in column 3.3.1: "enhancement of in-liquid sterilization effect by pH control" of the nonpatent reference 1.

For a similar reason, in Embodiment 1, use is made of water, various medicinal liquids and washing liquids whose pH value is 4.5 or below.

When the configuration includes the above gas fluid regulating valve 37, the regulation of rare gas flow rate by the gas fluid regulating valve 37 facilitates the increase or decrease of the length of the plasma jet generated by the plasma jet applying means 4 and the changing of the intensity of plasma jet application. Consequently, coping with various morphologies of an affected area during treatment can be facilitated.

The location to which the gas fluid regulating valve 37 is attached may be the inside or outside of the syringe 2 and is not particularly limited.

Figure 7:
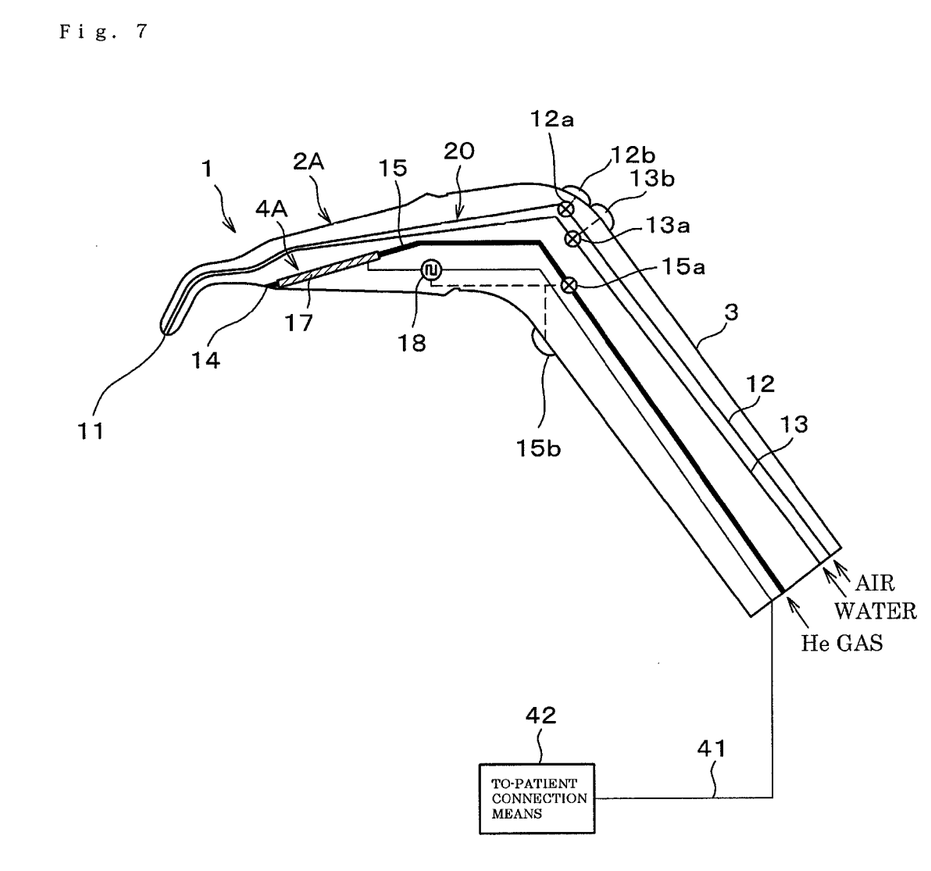
FIG. 7 is a schematic configuration view of a syringe-shaped dental clinical apparatus according to Embodiment 1 fitted with a one-electrode plasma jet applying means.

FIG. 7 shows a syringe 2A being a modified form of the syringe 2 of FIG. 1. Through the syringe 2A and the syringe 2 of FIG. 1, like numerals are used to indicate like elements, and duplicate description is avoided.

The basic configuration of the syringe 2A of FIG. 7 is the same as that of the syringe 2 of FIG. 1. The syringe 2A is characterized by the employment of a one-electrode plasma jet applying means 4A in place of the plasma jet applying means 4.

Figure 8:
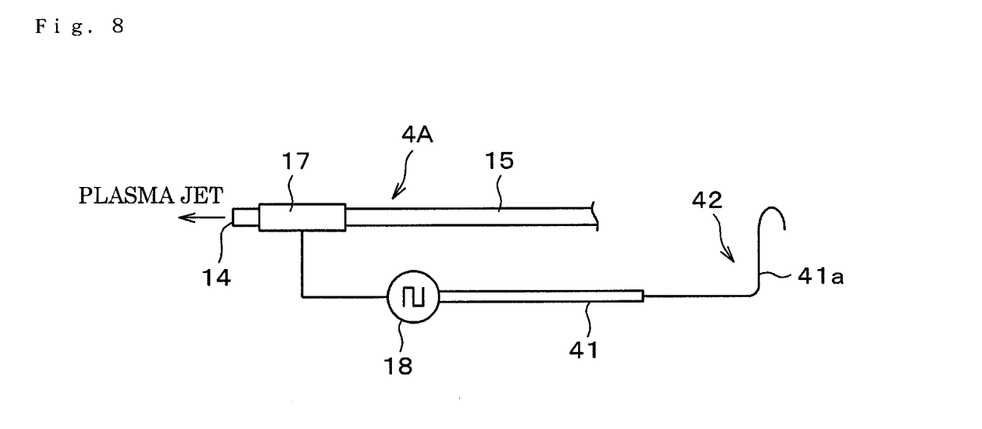
FIG. 8 is an enlarged explanatory view of a one-electrode plasma jet generating means included in the dental clinical apparatus of FIG. 7.

Illustratively in the plasma jet applying means 4A, referring to FIGS. 7 and 8, an electrode 17 functioning as a high-voltage electrode is disposed on a rare gas tube 15 through which, for example, gaseous helium as one of rare gases flows. A low-frequency high-voltage power supply 18 capable of outputting, for example, about 10 kHz-10 kV at its one terminal is connected to the electrode 17. The other terminal side of the low-frequency high-voltage power supply 18 is drawn out through a connection cable 41 to the patient side, and the end thereof is provided with a to-patient connection means 42.

As the to-patient connection means 42, there can be mentioned an arrangement in which referring to FIG. 8, for example, the covering of an end portion of the connection cable 41 is removed to thereby form an exposed electric wire portion 41a and the exposed electric wire portion 41a is curved to a circular arc and hung on a finger or the like of the patient. The exposed electric wire portion 41a may be wound around a hand or the like of the patient.

Namely, the plasma jet applying means 4A employs an arrangement in which grounding is effected by connecting the other terminal side of the low-frequency high-voltage power supply 18 to the patient.

The configuration is made so that dielectric barrier electric discharge is performed in the rare gas tube 15 provided with the electrode 17 to thereby generate plasma and that the generated plasma is emitted from the plasma jet application orifice 14 and applied to an affected area during treatment.

As the rare gas tube 15, use can also be made of a metal tube of, for example, SUS. In that event, in the rare gas tube 15 provided with the one electrode 17, electric discharge without dielectric barrier can be performed to thereby generate plasma and the generated plasma can be emitted from the plasma jet application orifice 14 and applied to an affected area during treatment.

With respect to the dielectric barrier electric discharge and electric discharge without dielectric barrier, reference can be made to the description relating to LF microplasma jet appearing in column 2.1.1, etc. of the nonpatent reference 1.

Naturally, the above configuration of the plasma jet application orifice 14 fitted with tip nozzle 22 shown in FIG. 3 and configuration of the plasma jet application orifice 14 fitted with tip nozzle 23 shown in FIG. 4 can also be employed in the syringe 2A of FIG. 7. In the employment of these, the same action and effect as mentioned above can be exerted.

Figure 9:
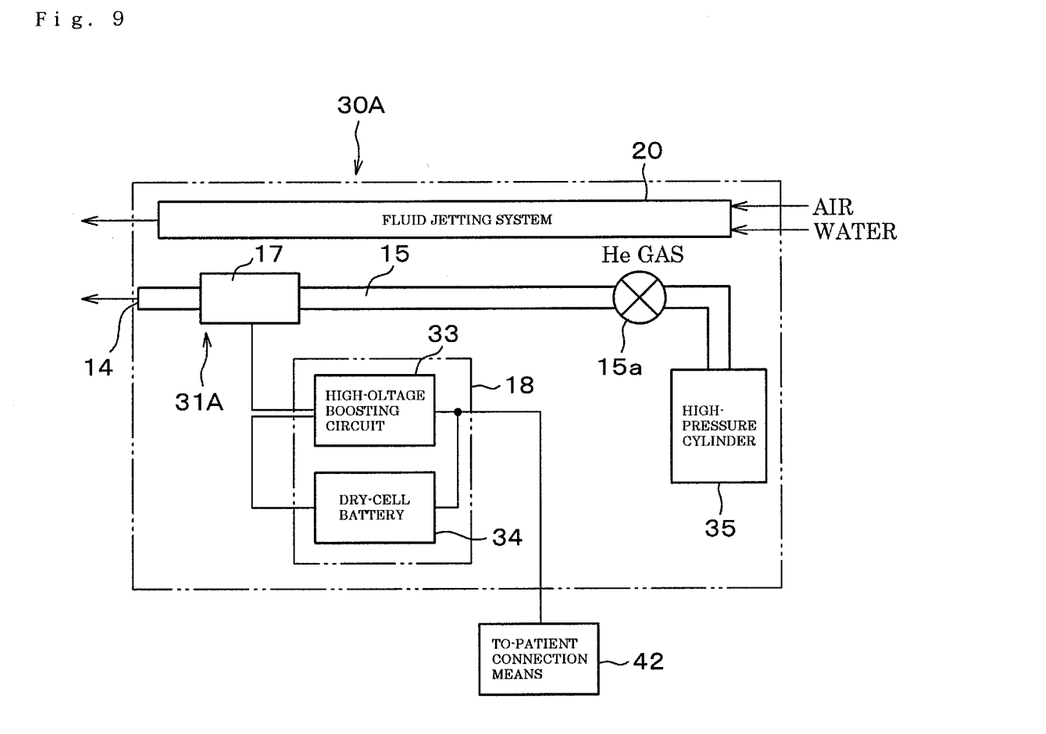
FIG. 9 is a schematic configuration view of a one-electrode plasma jet applying means of cordless structure included in a dental clinical apparatus according to Embodiment 1.

Now, referring to FIG. 9, a syringe 30A having the plasma jet applying means 4A changed to the same cordless structure as in FIG. 5 will be briefly described.

The syringe 30A includes a main body 32 of, for example, hair dryer morphology having not only the above-mentioned fluid jetting system 20 assembled therein but also a plasma jet applying means 31A fitted thereto.

In the plasma jet applying means 31A, an electrode 17 is disposed on the same rare gas tube 15 as mentioned above. A low-frequency high-voltage power supply 18 including a high voltage boosting circuit 33 capable of outputting, for example, about 10 kHz-10 kV and a dry-cell battery 34 capable of outputting DC 9V is connected to the electrode 17, so that low-frequency high-voltage is applied to the electrode 17. The other terminal side of the low-frequency high-voltage power supply 18 is drawn out through a connection cable 41 to the patient side, and the end thereof is provided with a to-patient connection means 42.

The syringe 30A equipped with the plasma jet applying means 31 with a cordless structure of the above arrangement does not need to connect a rare gas supply piping to the rare gas tube 15 of the plasma jet applying means 31A, apart from the piping to the fluid jetting system 20, so that there can be provided a simple apparatus capable of generating a plasma jet to be applied to an affected area during treatment and treating the same by use of the syringe 30A alone.

Figure 10:
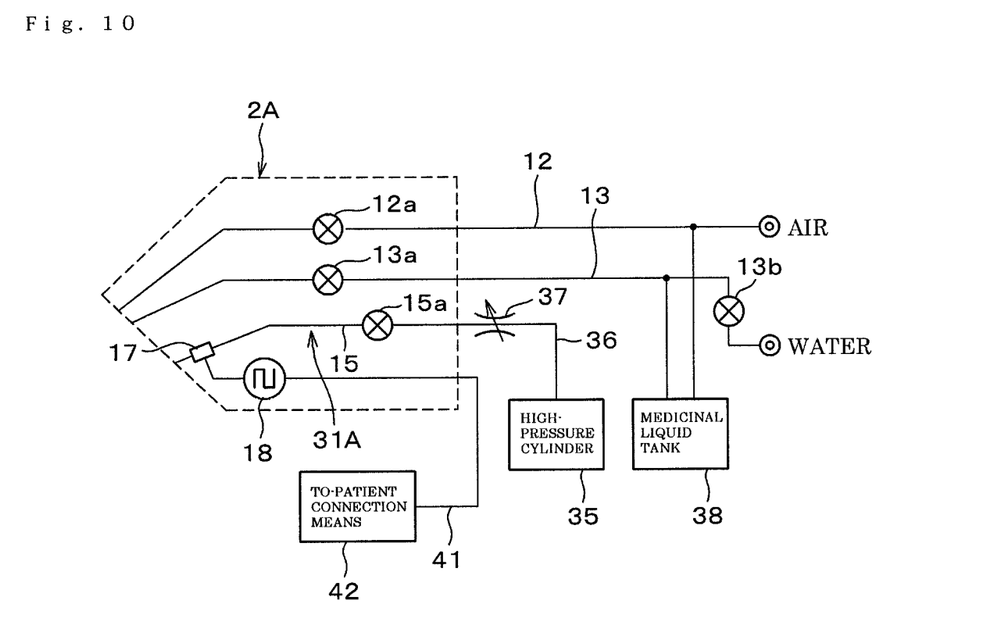
FIG. 10 is a schematic configuration view of a dental clinical apparatus including a one-electrode plasma jet applying means according to Embodiment 1, additionally provided with a gas fluid regulating valve.

FIG. 10 shows a schematic example of arrangement in which in the same fashion as in FIG. 6, a gas fluid regulating valve 37 is fitted to the midstream of a supply conduit 36 from the high-pressure cylinder 35 for supply of a rare gas to the rare gas tube 15 of the syringe 2A of FIG. 7.

When the configuration includes the above gas fluid regulating valve 37, as mentioned above, the regulation of rare gas flow rate by the gas fluid regulating valve 37 facilitates the increase or decrease of the length of the plasma jet generated by the plasma jet applying means 4. Consequently, coping with various morphologies of an affected area during treatment can be facilitated.

Furthermore, the dental clinical apparatus 1 according to Embodiment 1 can have an optical fiber 92 housed therein, as in Embodiment 4 to be described hereinafter, so that an affected area during treatment can be exposed to light.

The employment of this configuration can provide a dental clinical apparatus 1 capable of enhancing the wettability of a tooth surface and thus effecting a photopolymerization increasing the adhesion strength of a resin by a combination of light with plasma jet.

Still further, the dental clinical apparatus 1 according to Embodiment 1 can have a piping 102 for vacuum suctioning fitted to the apparatus main body 82 in addition to the plasma jet generating means, as in Embodiment 5 to be described hereinafter.

The employment of this configuration can provide a dental clinical apparatus 1 capable of, while suctioning saliva and dust from the oral cavity by vacuum, enhancing the wettability of an affected area during treatment and also sterilizing the same by a combination of plasma jet with vacuum suctioning.

EMBODIMENT 2

The dental clinical apparatus 51 according to Embodiment 2 of the present invention will be described below with reference to FIG. 11.

Figure 11:
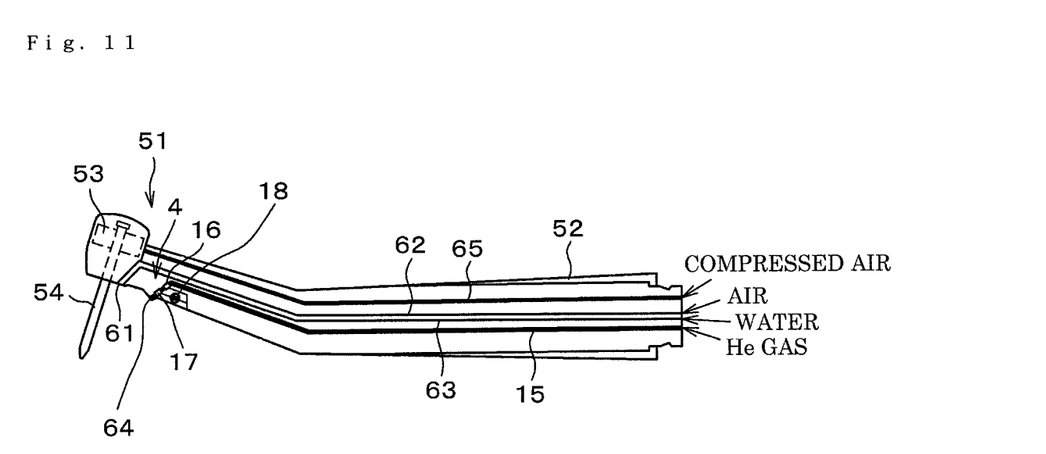
FIG. 11 is a schematic configuration view of a cutting-tool-shaped dental clinical apparatus according to Embodiment 2 of the present invention.

Referring to FIG. 11, the dental clinical apparatus 51 according to Embodiment 2 is in the form of a cutting tool comprising a handpiece main body 52, as an instrument, composed mainly of a hand-graspable metallic material bent and formed into an approximately inverted ←-shape and, rotatably fitted to the distal end thereof, a cutting bar 54 with blade 53. The handpiece main body 52 is characterized in that the same thereinside is fitted with the 2-electrode plasma jet applying means 4 as mentioned above capable of applying to an affected area during treatment of a tooth or the like a plasma jet based on a rare gas, such as gaseous helium or gaseous argon, exhibiting a low dielectric breakdown voltage under atmospheric pressure, which plasma jet has the capabilities of enhancing the wettability of an affected area during treatment and sterilizing the same and the like.

The dental clinical apparatus 51 according to Embodiment 2 can find application in a dental turbine, a dental micromotor or scaler, or the like.

The handpiece main body 52 is provided, on its distal end side and in the vicinity of the cutting bar 54, with an emission orifice 61 for air and water (or a medicinal liquid, a washing liquid such as distilled water, etc.). The handpiece main body 52 is further provided with an air conduit 62 and a liquid conduit 63 both extending from the proximal end side of the handpiece main body 52 through the interior thereof to the emission orifice 61. Accordingly, air is supplied through the air conduit 62 to the emission orifice 61, and selective supply of water, a medicinal liquid, a washing liquid or the like is conducted through the liquid conduit 63 to the emission orifice 61.

Therefore, there are provided means for selective emission of a spray of water, water with air or water-air mixture, emission of a medicinal liquid and emission of a washing liquid from the emission orifice 61 to an affected area during treatment.

The same plasma jet applying means 4 as mentioned above is housed in the handpiece main body 52, so that from a plasma jet application orifice 64 disposed in the vicinity of the emission orifice 61 in the handpiece main body 52, a plasma jet is applied to the distal end of the cutting bar 54 in the same manner as in the case of water or the like emitted from the emission orifice 61.

Further, for example, a power transmission system 65 for rotating the blade 53 of the cutting bar 54 is housed in the handpiece main body 52.

The power transmission system 65 is, for example, configured so that compressed air is fed to the blade 53 so as to rotate the blade 53 at a high speed and exhaust air is ejected through a conduit not shown to the proximal end of the handpiece main body. There can be mentioned a configuration such that the cutting bar 54 is detachably inserted in the rotating center shaft of the blade to thereby rotate the cutting bar 54 at a high speed. Further, there can be mentioned another configuration in which the cutting bar 54 is rotated using a motor and power transmission means, and the like. However, these belong to heretofore known technology, so that description is not made herein.

With respect to a dental clinical apparatus employed in the enlarging of the root canal, a plasma jet can be applied along the cutting bar 54 by disposing the plasma jet application orifice 64 in the vicinity of the root portion of the cutting bar 54 so as to facilitate the application of a plasma jet into the root canal and arranging the same substantially coaxially with the cutting bar 54.

The dental clinical apparatus 51 according to Embodiment 2 is capable of not only naturally performing the cutting treatment of an affected area during treatment by the rotation of the cutting bar 54 but also, as in Embodiment 1, generating a plasma jet in the rare gas tube 15 between the two electrodes 16,17, emitting the generated plasma jet from the plasma jet application orifice 69 and applying the plasma jet to the affected area during treatment so as to enhance the wettability of the affected area during treatment for resin filling and sterilize the affected area during treatment.

Figure 12:
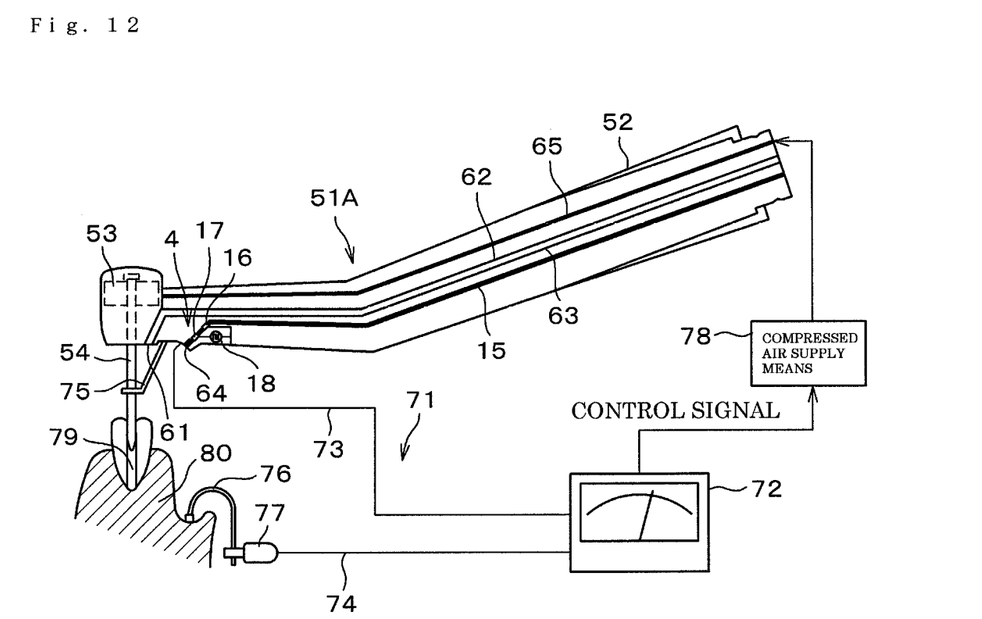
FIG. 12 is a schematic configuration view of a cutting-tool-shaped dental clinical apparatus according to Embodiment 2 combined with a root canal length measuring means.

FIG. 12 shows a dental clinical apparatus 51A comprising the same handpiece main body 52 as in the dental clinical apparatus 51 and, added thereto, a root canal length measuring means 71 for measuring the length of the root canal.

The root canal length measuring means 71 will be briefly described. The root canal length measuring means 71 includes a main body of root canal length meter 72 from which two leads 73,74 extend. One of the leads 73 is connected to a contact maker 75 fitted to the housing of the handpiece main body 52. The other lead 74 is connected to an electrode terminal 76 brought into contact with, for example, the gums 80 or the like by means of a connector 77 such as a clamp.

During the enlarging treatment of the root canal 81 of a tooth, the length of the root canal is measured by the main body of root canal length meter 72 by the use of a change of resistance between the contact maker 75 and the electrode terminal 76.

In the dental clinical apparatus 51A, the main body of root canal length meter 72 is configured so as to send a control signal for changing the driving force (rate of compressed air fed) to a compressed air supply means 78 for feeding the compressed air for rotating the blade 53 to the power transmission system 65 in accordance with the measurement value of the root canal length, thereby regulating the rotation of the cutting bar 54.

In this Embodiment, the power transmission system 65 uses compressed air. Instead, the cutting bar 54 can be rotated using a motor and a power transmission means. In this instance, the control of forward reverse rotation, low-speed rotation, adjustable-speed rotation or the like can be facilitated.

The dental clinical apparatus 51A of FIG. 12 not only can exert the same action and effect as in the use of the dental clinical apparatus 51 but also can appropriately correlate the operation of measuring the length of the root canal by the root canal length measuring means 71 with the operation of cutting an affected area during treatment by the cutting bar 54 with the result that the root canal 81 can be effectively treated.

Figure 13:
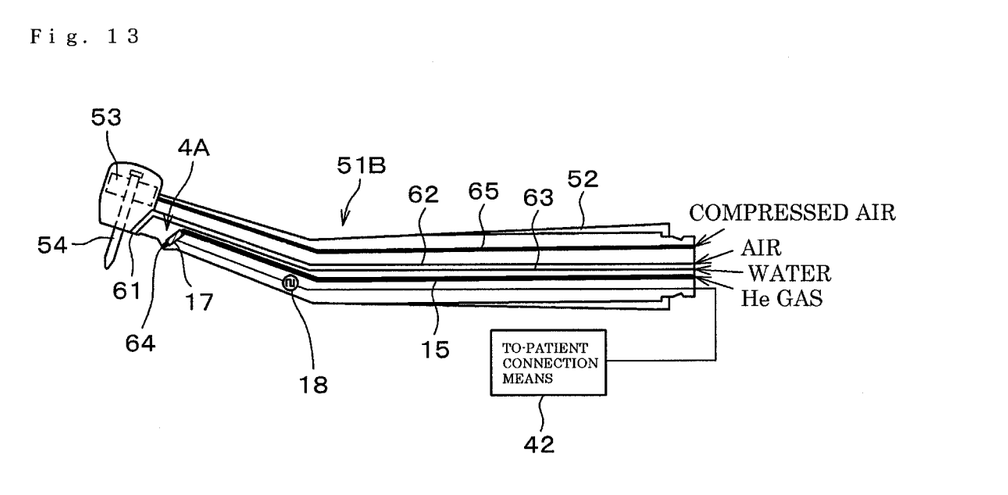
FIG. 13 is a schematic configuration view of another form of cutting-tool-shaped dental clinical apparatus according to Embodiment 2.

FIG. 13 shows a dental clinical apparatus 51B with substantially the same configuration as that of the dental clinical apparatus 51 of FIG. 11. However, the dental clinical apparatus 51B is characterized by being fitted with the same one-electrode plasma jet applying means 4A as employed in the syringe 2A of FIG. 7.

This dental clinical apparatus 51B is capable of not only naturally performing the cutting treatment of an affected area during treatment by the rotation of the cutting bar 54 but also generating a plasma jet in the rare gas tube 15 in the vicinity of the electrode 17, emitting the generated plasma jet from the plasma jet application orifice 64 and applying the emitted plasma jet to an affected area during treatment so as to enhance the wettability of the affected area during treatment for resin filling and sterilize the affected area during treatment.

Naturally, each of the dental clinical apparatus 51 of FIG. 11, the dental clinical apparatus 51A of FIG. 12 and the dental clinical apparatus 51B of FIG. 13 can employ the above configuration of plasma jet application orifice 14 with tip nozzle 22 shown in FIG. 3 and configuration of plasma jet application orifice 14 with tip nozzle 23 shown in FIG. 4. When these are employed, the same action and effect as mentioned above can be exerted.

Furthermore, each of the dental clinical apparatuses 51, 51A and 51B according to Embodiment 2 can have an optical fiber 92 housed therein, as in Embodiment 4 to be described hereinafter, so that an affected area during treatment can be exposed to light.

The employment of this configuration can provide a dental clinical apparatus 1 capable of not only illuminating an affected area during treatment but also enhancing the wettability of a tooth surface and thus effecting a photopolymerization increasing the adhesion strength of a resin by a combination of light with plasma jet.

The employment of this configuration makes it feasible to enhance the wettability of a tooth surface and thus effect a photopolymerization increasing the adhesion strength of a resin by a combination of light with plasma jet.

EMBODIMENT 3

The plasma jet applying device for dentistry 81 according to Embodiment 3 of the present invention will be described below with reference to FIG. 14. Through the syringe 2 of FIG. 1 and the plasma jet applying device for dentistry 81, like numerals are used to indicate like elements, and duplicate description is avoided.

Figure 14:
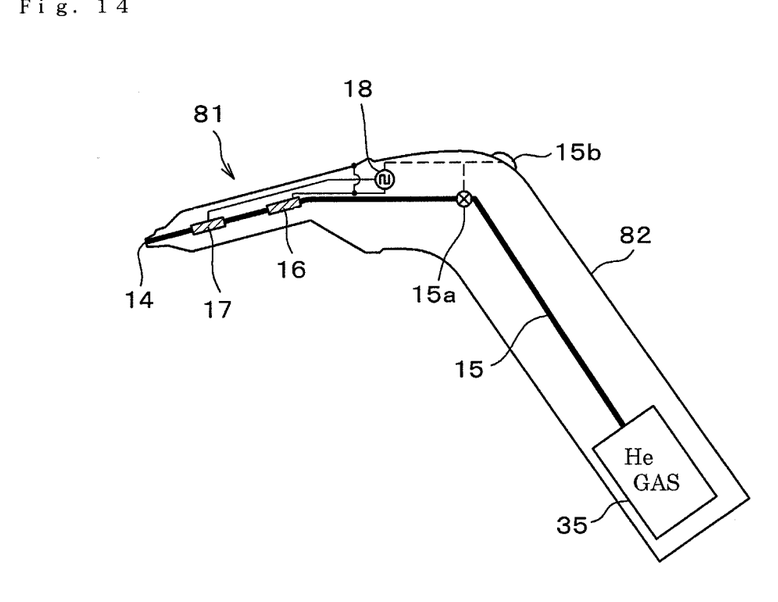
FIG. 14 is a schematic configuration view of a plasma jet applying device for dentistry according to Embodiment 3 of the present invention.

The plasma jet applying device for dentistry 81 of FIG. 14 is characterized by including the same device main body 82 composed mainly of a hand-graspable metallic material bent and formed into an approximately ←-shape as in the syringe 2 of FIG. 1, which device main body 82 is fitted with the two-electrode plasma jet applying means 4 as mentioned above capable of applying to an affected area during treatment of a tooth or the like a plasma jet based on a rare gas, such as gaseous helium or gaseous argon, exhibiting a low dielectric breakdown voltage under atmospheric pressure, which plasma jet has the capabilities of enhancing the wettability of an affected area during treatment and sterilizing the same and the like. The device main body 82 further has the same high-pressure cylinder 35 as mentioned above assembled therein to thereby realize a cordless configuration rendering the device portable.

The plasma jet applying device for dentistry 81 according to Embodiment 3, as mentioned in Embodiment 1, is capable of generating a plasma jet in the rare gas tube 15 between the two electrodes 16,17 in the plasma jet applying means 4, emitting the generated plasma jet from the plasma jet application orifice 14 and applying the emitted plasma jet to an affected area during treatment so as to enhance the wettability of the affected area during treatment for resin filling and sterilize the affected area during treatment.

Moreover, the plasma jet applying device for dentistry 81 according to Embodiment 3 has the advantage that it can be cordless and can be freely carried by accommodating a high-pressure cylinder 35 containing gaseous helium or the like inside the device main body 82 and using a dry-cell battery 34 as a low-frequency high-voltage power supply 18 as shown in FIG. 5, thereby simplifying and facilitating the use thereof in combination with any of the existing syringes and cutting tools for dental treatment.

Below, a plasma jet applying device for dentistry 81A being a modified form of that of Embodiment 3 will be described below with reference to FIG. 15.

Figure 15:
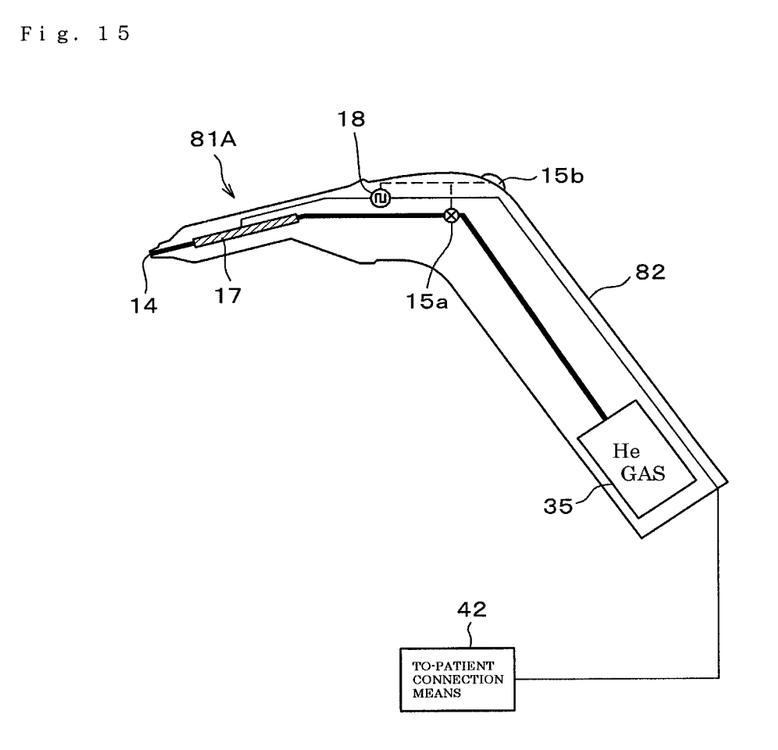
FIG. 15 is a schematic configuration view of another form of plasma jet applying device for dentistry according to Embodiment 3.

The plasma jet applying device for dentistry 81A of FIG. 15 is characterized by including the same device main body 82 composed mainly of a hand-graspable metallic material bent and formed into an approximately ←-shape as in the syringe 2 of FIG. 1, which device main body 82 is fitted with the same one-electrode plasma jet applying means 4A as mentioned above capable of applying to an affected area during treatment of a tooth or the like a plasma jet based on a rare gas, such as gaseous helium or gaseous argon, exhibiting a low dielectric breakdown voltage under atmospheric pressure, which plasma jet has the capabilities of enhancing the wettability of an affected area during treatment and sterilizing the same and the like. The device main body 82 further has the same high-pressure cylinder 35 as mentioned above assembled therein to thereby realize a cordless configuration rendering the device portable.

In the use of this plasma jet applying device for dentistry 81A, as in the use of the plasma jet applying device for dentistry 81, a plasma jet can be emitted and applied to an affected area during treatment so as to enhance the wettability of the affected area during treatment for resin filling and sterilize the affected area during treatment.

Moreover, as mentioned with respect to the plasma jet applying device for dentistry 81, this plasma jet applying device for dentistry 81A has the advantage that it can be cordless and can be freely carried, thereby simplifying and facilitating the use thereof in combination with any of the existing syringes and cutting tools for dental treatment.

EMBODIMENT 4

The plasma jet applying device for dentistry 91 according to Embodiment 4 of the present invention will be described below with reference to FIG. 16. Through the plasma jet applying device for dentistry 81 of FIG. 14 and the plasma jet applying device for dentistry 91, like numerals are used to indicate like elements, and duplicate description is avoided.

The plasma jet applying device for dentistry 91 according to Embodiment 4 of the present invention is characterized by including the structure of the plasma jet applying device for dentistry 81 of FIG. 14 having its device main body 82 fitted with an optical fiber 92 with light-coupled switch 94 configured to perform light irradiation from the vicinity of the plasma jet application orifice 14 toward an affected area during treatment, the device main body 82 further having a light irradiation switch 93 added thereto.

In the use of this plasma jet applying device for dentistry 91 according to Embodiment 4, as in the use of the plasma jet applying device for dentistry 81 of FIG. 14, the generated plasma jet can be emitted from the plasma jet application orifice 14 and applied to an affected area during treatment so as to enhance the wettability of the affected area during treatment for resin filling and sterilize the affected area during treatment.

In addition, as the optical fiber 92 is attached so as to be able to perform light irradiation toward an affected area during treatment, the dental clinical apparatus 91 can be one capable of enhancing the wettability of a tooth surface and thus effecting a photopolymerization increasing the adhesion strength of a resin by a combination of light (especially light with a wavelength capable of hardening a resin as a dental restorative material) with plasma jet application.

More specifically, as the dental restorative material, there can be mentioned a resin hardenable by irradiation with visible light. The dental clinical apparatus 91 can apply a plasma jet in the treatment prior to filling a tooth with the resin. Applying the plasma jet to a tooth allows the tooth surface to have a functional group to thereby increase the activity of the surface and enhance the wettability thereof. Thus, the adhesion strength of the resin can be increased. Further, the plasma jet couples with smears adhering to the tooth surface, so that a washing effect can be expected.

EMBODIMENT 5

The plasma jet applying device for dentistry 101 according to Embodiment 5 of the present invention will be described below with reference to FIG. 17. Through the plasma jet applying device for dentistry 91 of FIG. 16 and the plasma jet applying device for dentistry 101, like numerals are used to indicate like elements, and duplicate description is avoided.

Figure 16:
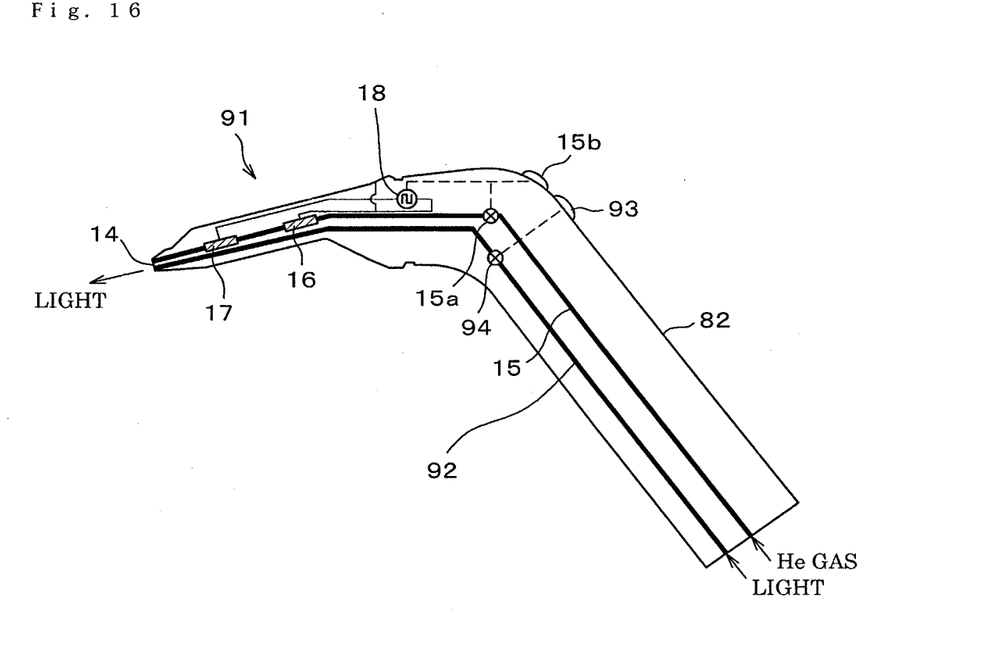
FIG. 16 is a schematic configuration view of a plasma jet applying device for dentistry according to Embodiment 4 of the present invention.
Figure 17:
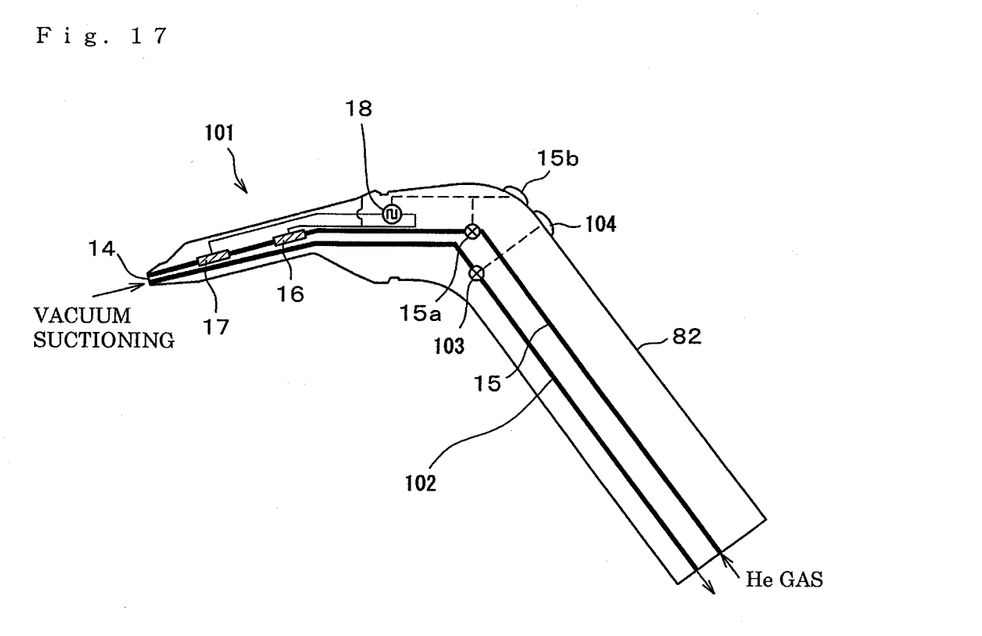
FIG. 17 is a schematic configuration view of a plasma jet applying device for dentistry according to Embodiment 5 of the present invention.

The plasma jet applying device for dentistry 101 according to Embodiment 5 of the present invention is characterized by disposing a piping 102 for vacuum suctioning in the device main body 82 in place of the optical fiber 92 included in the plasma jet applying device for dentistry 91 of FIG. 16, causing one end of the piping 102 to face the vicinity of the plasma jet application orifice 14 and connecting the other end side of the piping 102 to a vacuum suctioning source, such as a pump, not shown. In FIG. 17, numeral 103 denotes a vacuum on-off valve, and numeral 104 denotes a vacuum switch.

The plasma jet applying device for dentistry 101 according to Embodiment 5 of the present invention is capable of, while suctioning saliva and dust from the oral cavity by vacuum, enhancing the wettability of an affected area during treatment and also sterilizing the same by the plasma jet application.

The feature of the plasma jet generating means for use in the dental clinical apparatus of the present invention is widely applicable to a variety of dental treatment appliances, such as a photopolymerization unit equipped with an optical fiber and a light emitting source to thereby photopolymerize resins, a tooth surface washing appliance and a perforating appliance.

The invention claimed is:
1. A dental clinical apparatus for dentistry, comprising:
a syringe including a hand-graspable main body having a proximal end and a distal end configured to be positioned at a tooth or gum portion during dental treatment;
an emission orifice provided at the distal end of the main body;
a fluid jetting system provided in the main body, the fluid jetting system including an air conduit and a liquid conduit that both extend from the proximal end of the main body and through the interior of the main body to the emission orifice so that air and a liquid comprising at least one of water, a medicinal liquid, and a washing liquid are selectively conducted from the proximal end of the main body to and from the emission orifice;
a plasma jet generating unit including
a rare gas tube for feeding a rare gas exhibiting a low dielectric breakdown voltage under atmospheric pressure;
a low-frequency high-voltage power supply; and
an electric discharge part with a two-electrode structure including a first electrode and a second electrode disposed, respectively, on an upstream side and a downstream side at an outer circumference of the rare gas tube, the first electrode being connected to a grounding side of the power supply and the second electrode being connected to a high-voltage side of the power supply, so that an electric discharge is generated between the first and second electrodes in the rare gas flowing through the rare gas tube and a plasma jet is formed by the electric discharge; and
a plasma jet application orifice disposed in the vicinity of the emission orifice in the main body, the plasma jet application orifice being configured to apply the plasma jet toward the tooth or gum portion during dental treatment.

2. The dental clinical apparatus according to claim 1, wherein the syringe is further configured to output air, water, a medicinal liquid, a washing liquid, and light individually or in a combination of a plurality thereof from the emission orifice.

3. The dental clinical apparatus according to claim 1, wherein the apparatus further comprises a washing liquid supply device supplying a washing liquid to the affected area after elimination of a decay lesion from a tooth surface.

4. The dental clinical apparatus according to claim 1, wherein the apparatus is configured to be used in treatment of a root canal interior after elimination of a decay lesion from the tooth.

5. The dental clinical apparatus according to claim 4, wherein the apparatus further comprises a de-smearing treatment device configured to perform de-smearing treatment of the root canal interior after elimination of the decay lesion from the tooth so that the plasma jet is applied to the root canal interior after or during the treatment by the de-smearing treatment device.

6. The dental clinical apparatus according to claim 5, wherein the de-smearing treatment device is configured to feed a de-smearing medicinal liquid to the affected area during treatment so as to dissolve away any smear plug and thereafter feed a washing liquid thereto to thereby wash the affected area.

7. The dental clinical apparatus according to claim 2 or 6, wherein a liquid supplied as the water, the medicinal liquid such as a de-smearing medicinal liquid or the washing liquid exhibits a pH value of 4.5 or below.

8. The dental clinical apparatus according to claim 1, wherein the plasma jet application orifice includes a detachably replaceable distal end nozzle.

9. The dental clinical apparatus according to claim 1, wherein the plasma jet application orifice is adaptable to receive at least one of plurality of nozzles each of which has a different nozzle size.

10. The dental clinical apparatus according to claim 1, wherein the rare gas is gaseous helium or gaseous argon.

11. The dental clinical apparatus according to claim 10, wherein the rare gas tube is provided with a gas fluid regulating valve.

* * * * *